(12) United States Patent
Leath (10) Patent No.: US 7,626,149 B2
(45) Date of Patent: Dec. 1, 2009

(54) NON-INVASIVE SENSOR AND METHOD OF USE

(75) Inventor: Shane Richard Leath, Rototuna (NZ)

(73) Assignee: AgResearch Limited, Hamilton (NZ)

( * ) Notice: Subject to any disclaimer, the term of this patent is extended or adjusted under 35 U.S.C. 154(b) by 0 days.

(21) Appl. No.: 11/673,928

(22) Filed: Feb. 12, 2007

(65) Prior Publication Data

US 2007/0188372 A1      Aug. 16, 2007

Related U.S. Application Data

(63) Continuation of application No. PCT/NZ2005/000205, filed on Aug. 12, 2005.

(51) Int. Cl.
*H05B 6/64* (2006.01)
*G01V 3/10* (2006.01)

(52) U.S. Cl. ...................... 219/703; 324/339

(58) Field of Classification Search .......... 219/703, 219/769, 679, 710, 716; 324/339, 335, 338, 324/340, 341, 356, 366, 367, 643; 343/753; 73/73; 342/50, 26, 99, 56, 104, 26 R, 372, 342/418, 461; 340/572.1
See application file for complete search history.

(56) References Cited

U.S. PATENT DOCUMENTS

| 4,716,360 | A | * | 12/1987 | Pakulis .................. 324/640 |
| 4,727,311 | A | * | 2/1988 | Walker .................. 324/640 |
| 5,028,929 | A | | 7/1991 | Sand et al. |
| 5,055,849 | A | * | 10/1991 | Andersson et al. ........ 342/104 |
| 6,218,842 | B1 | * | 4/2001 | Bittar et al. .............. 324/339 |
| 2002/0014966 | A1 | * | 2/2002 | Strassner et al. ........ 340/572.1 |

FOREIGN PATENT DOCUMENTS

| WO | WO98/01747 | 1/1998 |
| WO | WO2004/055504 | 7/2004 |

* cited by examiner

*Primary Examiner*—Quang T Van
(74) *Attorney, Agent, or Firm*—McAndrews, Held & Malloy, Ltd.

(57) ABSTRACT

A method of temperature and/or composition measurement of an at least partially aqueous target (6) using a system (1) including; a transmitter and receiver mechanism (2) including one or more transmitting (3) and receiving antenna(e) (4); signal processor (5), capable of calculating the attenuation of the transmitted signal; the method including the steps of; irradiating a target (6) with a plurality of electromagnetic radiation signals including a first signal with a frequency in the microwave/UHF spectrum, and a second signal with a frequency in the radio frequency (RF) spectrum; receiving an attenuated signal transmitted though the target (6); calculating the attenuation of the transmitted signal with the signal processor (5).

6 Claims, 7 Drawing Sheets

NON-INVASIVE SENSOR AND METHOD OF USE

CROSS REFERENCE TO RELATED APPLICATIONS

This application is a continuation of International Application No. PCT/NZ2005/000205, having an international filing date of Aug. 12, 2005,entitled "Non-Invasive Temperature and Composition Sensor for Partially Aqueous Targets". International Application No. PCT/NZ2005/000205 claimed priority benefits, in turn, from New Zealand Patent Application No. 534,673 filed Aug. 12, 2004. International Application No. PCT/NZ2005/000205 is hereby incorporated by reference herein in its entirety.

TECHNICAL FIELD

The present invention relates to a non-invasive sensor and method of use primarily for temperature measurement, though also applicable to composition sensing, including fat percentage.

BACKGROUND ART

Non-invasive temperature measurement of frozen/near frozen organic matter using single-frequency microwave radiation is well documented. Such techniques are particularly useful in the transport and storage chain between producer and consumer to monitor the temperature of frozen produce. Standard operating practices and regulatory/legislative requirements in the food industry require frozen produce, such as meat, to be frozen below a prescribed temperature before and during shipment along the length of the cold chain. Arrival of insufficiently cooled produce at the recipient destination casts doubt on temperature maintenance (and measurement procedures) of each stage in the chain. To limit such liability, the various parties in the cold chain traditionally undertake random monitoring tests, typically via an invasive process of drilling the produce and manually inserting a temperature probe.

Such techniques are clearly unsatisfactory as they are:
Time-consuming and labour intensive,
Potentially inaccurate unless performed carefully,
Unable to check every item and thus problem produce may escape detection,
Non-automated, and
Wasteful; the tested produce typically requires re-sealing, re-packing, down grading or disposal.

Microwave temperature measurement permits a rapid, non-invasive, potentially automated method of testing all the frozen produce supplied, as described in the applicant's earlier patent applications including PCT/NZ03/00279 incorporated herein by reference. Nevertheless, known microwave temperature measurement techniques still suffer from disadvantages, primarily related to the intrinsic physical characteristics of microwave interactions with ice and water.

The passage of microwave radiation through a given material is attenuated according to a function dependent on both material temperature and the microwave frequency. Moreover, the microwave attenuation diminishes significantly at sub-freezing point temperatures resulting in the frozen material effectively becoming transparent to microwave radiation.

This disproportional attenuation of microwaves by water rather than ice is observed in domestic microwave ovens during heating of frozen food. The outside layer of ice slightly absorbs microwaves and melts to form water which consequently absorbs almost all the subsequent microwave energy leaving little energy to heat the internal ice. The outer layer of the food is thus left cooked, while the centre remains frozen.

Furthermore, it has been determined that for the temperatures used in the food chain (ranging from 0° C. to −30° C.), the ratio of the water and ice composition (or 'ice fraction') present in meat or other similarly water-rich organic produce is constant for a given temperature. Combining the two properties (i.e. the disproportionate transparency to microwaves of ice compared to water and the correlation of the ice fraction and temperature) provided the basis for a non-invasive temperature measurement device utilising a single microwave frequency.

Such systems are capable of measuring the temperature of a single frozen meat carton, for example, by measuring the unabsorbed energy of a single microwave frequency passed through the meat carton and correlating with remaining unfrozen water to calculate the temperature.

However, the typical microwave frequencies (e.g. 2.4 GHz) employed in such systems cannot penetrate more than approximately 200 mm of water. Thus for meat cartons or the like, this restricts instantaneous measurements to single cartons. This poses disadvantages in measurement throughput as it would be typically desirable in most meat processing plants and subsequent stages in the cold chain to measure a whole pallet of cartons without un-stacking the individual cartons.

The electromagnetic energy attenuated by a material is given by the formula:

$$P_z = P_o e^{-2\alpha z} \quad (1)$$

where P is the residual power
$\alpha$ is the attenuation factor (frequency and material dependent)
o indicates the initial condition, and
z indicates the equivalent depth of material (i.e. excluding any voids and non-material spaces)

Thus, it can be seen that simply increasing the power transmitted does not permit thicker layers of water/ice to be measured, although it does impact directly on the noise level and signal resolution.

Known microwave temperature measurement techniques are thus limited in their applications by thickness of the measured object. As previously discussed, this means for example that a pallet of cartoned frozen meat would require un-stacking before measurement of the individual cartons.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

The present invention provides a non-invasive temperature measurement and (optionally) composition sensing system and method of use. The present invention is particularly applicable for use with chilled or frozen organic produce stored and transported within typical cold chain temperatures.

According to one aspect, the present invention provides a system for temperature and/or composition measurement of an at least partially aqueous target including:

a transmitter and receiver mechanism including one or more transmitting and receiving antenna(e), said mechanism capable of irradiating said target with a plurality of electromagnetic radiation signals including a first and a second electromagnetic radiation signal of differing frequencies and receiving an attenuated signal transmitted though the target;

signal processing means, capable of calculating the attenuation of the transmitted signal;

characterised in that, said first signal has a frequency in the microwave/UHF spectrum, and said second signal has a frequency in the radio frequency (RF) spectrum.

As used herein, the terms microwave/UHF spectrum and radio frequency (RF) spectrum are defined as 100 MHz-500 GHz and 0.1 KHz-100 MHz respectively.

From Equation (1) it can be seen that reducing a allows a larger z to be penetrated for the same $P_z$ and $P_o$. Thus for a given thickness of target material the relationship between power, frequency and penetration can be optimised by carefully selecting the optimum frequency from a suitable frequency band.

Preferably, said first signal has a frequency between 200 MHz to 3.5 GHz and said second signal has a frequency between 0.1-10 KHz for meat thicknesses of 50 to 1200 mm thick.

It is recognised that the numerical definitions used by different parties for microwave and RF frequencies may differ from the above definitions. However, it will be appreciated that the present invention utilises the different physical attenuation by ice and water exhibited by the separate electromagnetic radiation signals to determine the target temperature and consequently, it is the frequencies that cover the absorption effects which are pertinent, and not a historical or academic definition of microwave or RF frequencies. Thus, as used herein, the term 'microwave' is used to denote both microwave signals and frequencies classified as ultra high frequency (UHF) signals.

Thus, according to a further aspect, the present invention provides a system for temperature measurement of an at least partially aqueous target including:

a transmitter and receiver mechanism including one or more transmitting and receiving antenna(e), said mechanism capable of irradiating said target with a plurality of electromagnetic radiation signals including a first and a second electromagnetic radiation signal of differing frequencies and receiving an attenuated signal transmitted though the target;

signal processing means, capable of calculating the attenuation of the transmitted signal;

characterised in that at said differing frequencies of the first and second signals;

absorption of said first signal by water is disproportionately higher than absorption by ice and absorption of said second signal by ice is disproportionately higher than absorption by water.

The use of signals from at least two separate portions of the EM spectrum provides a means (described more fully below) of overcoming the aforesaid microwave limitations in the penetrable depth of water present in the target by utilising the converse absorption characteristics of RF radiation with respect to ice and water, while also eliminating potential measurement error source arising from other typical target constituents such as fat and bone.

The present invention is described herein particularly with reference to the temperature measurement of chilled or frozen meat or the like. It should be understood that this is for exemplary purposes only and the invention is not so restricted. The present invention may also be used to determine the temperature of other substances and/or at least partially determine the composition of certain targets such as the fat percentage.

According to a further aspect, the present invention provides a system and method for measurement of non-frozen or frozen temperatures of a target material determined by selection of one or more said irradiating frequencies such that the corresponding attenuation for at least one corresponding target constituent(s) is substantially zero and/or constant, enabling temperature of a remaining constituent to be measured directly from the attenuation of the total transmitted signal received by the receiving antenna.

As used herein, the term 'target' includes, but is not limited to chilled, frozen, or near frozen meat (including poultry, lamb, beef, and pork), fish, cheese, butter, oils and vegetables.

As used herein, the terms 'partially aqueous target' includes any target with between 5 and 100% aqueous content. As the degree of microwave energy absorbed is dependent on the equivalent depth of water z present in the target (according to the equation (1)), the microwave frequency and power may be varied to accommodate targets of different aqueous content.

As used herein, the term 'signal processing means' includes, but is not limited to any device or system with data input/output and processing capacity, capable of calculating the signal attenuation, phase angle change, attenuation and/or polarisation from a comparison of the signal from the receiving antenna and the signal transmitted from the transmitter antenna. Preferably, the signal processing means is also capable of performing calculations according to one or more relationships defined herein, optionally with calibration input from known data sets. It will be appreciated that while convenient to automatically perform all the temperature calculations within the signal processing means, it is also possible to utilise further external processing/computing means and or even perform said calculations manually with reference to known data sets.

As previously discussed, the electromagnetic energy attenuated by a material is given by the formula:

$$P_z = P_o e^{-2\alpha z} \quad (1)$$

where P is the residual power

α is the attenuation factor (frequency and material dependent)

o indicates the initial condition, and z indicates the equivalent depth of material (i.e. excluding any voids and non-material spaces)

In the case of frozen meat compositions, the strict definitions of water fraction W and ice fraction I are respectively given as:

W=(mass of water)/(mass of water+ice+fat+protein+salts+ash)

and

I =(mass of ice)/(mass of ice+water+fat+protein+salts+ash), although the non-water/ice constituent fractions are often omitted from references to the ice and water fractions regarding their inter-relationship in temperature behaviour.

However, it is also known that the fat content in meat (also referred to as chemical lean (CL)) and oil in fish are also largely transparent to microwave radiation in a corresponding manner to ice.

To eliminate the effect of fat content of meat on the temperature predictions, a further variable requires measuring which is also independent of the fat content. In the present invention, this need has been resolved by utilisation of a further interaction absorption property of ice with electromagnetic radiation. In a comparable manner to the disproportionate absorption of microwaves by water in comparison to ice, radio frequency waves are disproportionably absorbed by ice compared to water.

Thus, the present invention uses microwaves to predict the amount of water in the target and RF waves to predict the amount of ice. These results are combined with established data on the ice/water ratio correlation with temperature to predict the target temperature according to the equations:

$$I \approx (W - 0.25S)\left[1 - \frac{T_f}{T}\right] \quad (2)$$

where
I is the Ice Fraction
W is the Water Fraction
S is the Solids Fraction (includes proteins, salts and ash)
$T_f$ is the Freezing Temperature, and
T is the Actual Temperature Rearranging this equation gives:

$$\frac{I}{(W - 0.25S)} \approx \left[1 - \frac{T_f}{T}\right] \quad (3)$$

As discussed above,
I ∝ Radio Frequency attenuation $\Delta_{RF}$,
W ∝ Microwave attenuation $\Delta_{Mw}$ And further

S ∝ (W+I)

Therefore $$\frac{\Delta_{RF}}{\Delta_{Mw}} \propto \left[1 - \frac{T_f}{T}\right]. \quad (4)$$

Consequently, it can be seen that the ratio of Radio Frequency attenuation $\Delta_{RF}$ to Microwave Frequency attenuation $\Delta_{MW}$ can be correlated to the temperature T of the target material, independently of the fat, oil, or solids content.

Thus, according to one aspect of the present invention there is provided a temperature measurement system as described above, wherein the instantaneous target temperature T is determined according to the relationship:

$$T \propto \left[\frac{T_f}{1 - \frac{\Delta_{RF}}{\Delta_{Mw}}}\right] \quad (5)$$

The proportional relationship in equation (5) may be replaced by an equivalence relationship through the addition of a calibration factor which may be target material, frequency, and/or geometry dependent. Further, a third frequency may be correlated to attenuation of EM energy by fat in the 0.1 to 110 MHz range (depending on the equivalent depth of meat target).

It will also be appreciated that if the target weight is known and if the water and ice fraction is known, it will be possible to calculate the target fat content according to the relationship:

Fat mass=Target Mass×[1−[W+I+S]]  (6)

and thus provides a means of checking the integrity of the fat determination performed by measuring the attenuation of three or more frequencies as described above.

The Fat Fraction (F) is defined as Fat Mass/Target Mass thus by rearranging equation (6) a composition balance may be obtained:

F+W+I=1−S  (7)

And since

S=β×(W+I)

and where β is a proportionality constant≈protein+salts+ash (typically 0.2–0.25 for bovine meat)

Then

F+(1+β)×[W+I]=1

Thus composition predictions may be made which are independent of temperature and mass of the target. It will also be appreciated that for material above zero degrees Celsius then the Ice Fraction is zero and the composition of non-frozen materials such as cheese, butter or oils maybe deduced.

Knowledge of the fat content of meat or CL, is of significant commercial value to meat processors. Contractual supply arrangements between meat processors and their customers often incorporate stringent tolerance values for meat CL, with punitive penalties for the supply of meat exceeding the defined parameters. The present invention may be used as a supplementary check to other conventional CL measurement processes employed, such as dual energy x-ray analysis (DXA) systems, or manual testing procedures. Alternatively, the present invention may be relied upon as the primary CL measurement technique, in addition to ensuring safe freezing temperatures are maintained for produce shipped from the plant. The characteristics of the microwave and RF technologies involved in the present invention provide a significant reduction in cost and environmental hazards over DXA analysis equipment, whilst offering speed, automation and accuracy advantages over manual CL testing methods.

Issues affecting the accuracy to the measured results include variations in the beam path travelled by the microwave and RF waves. Such errors are minimised in one embodiment, by transmitting said first and second signal from a common antenna along a co-axial beam axis. Although such a configuration eliminates geometric beam paths variations, it can add complexity to the transmitter as a single device is thus required to generate and transmit differing frequencies normally provided by separate devices.

This issue is addressed in an alternative embodiment wherein said first and second signals are transmitted from separate antennae along reciprocal beam axes from opposing sides of the target. To maintain the optimum correspondence between the first and second signal beam paths, the position and orientation of the first signal transmitting antenna and the second signal receiving antenna (and vice versa) should be substantially identical. This requirement may be addressed by combination transmitter/receiver assemblies. Positioning the transmitting and receiving antenna pairs in an orthogonal orientation such that the signal beams sweep the same volume of the target provides another viable configuration to minimise measurement errors.

Further it can be appreciated that the target could placed between a first antennae set, scanned at the first frequency, then moved to a new position between a second antennae set and scanned at the second frequency, where antennae sets incorporate any one of the embodiments discussed herein.

In a yet further embodiment, at least one transmitting and receiving antennae pair are orientated in a non-confronting, preferably co-axial arrangement, whereby the receiver receives a reflected signal from the target, not a transmitted signal. This provides the potential to measure individual units within a target such as individual meat cartons on a pallet.

The present invention thus provides a temperature measurement and composition analysis system enabling increased automation at meat processing plants and at subsequent stages in the cold chain, through automated temperature measuring of whole pallets of produce without damage by invasive tests or the need to unpack and test individual cartons.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
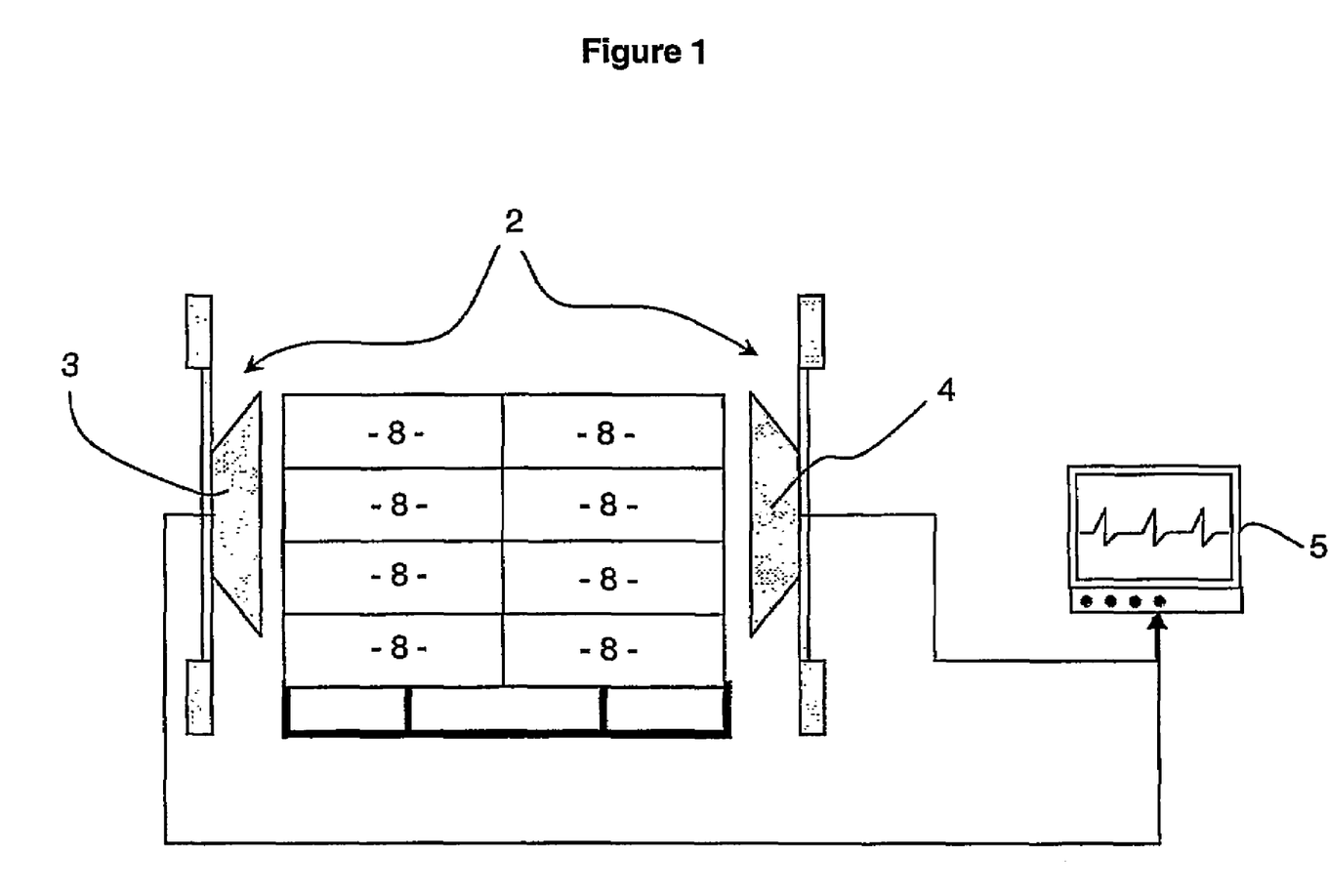
FIG. 1 Shows a schematic representation of a first preferred embodiment of the present invention.
Figure 2:
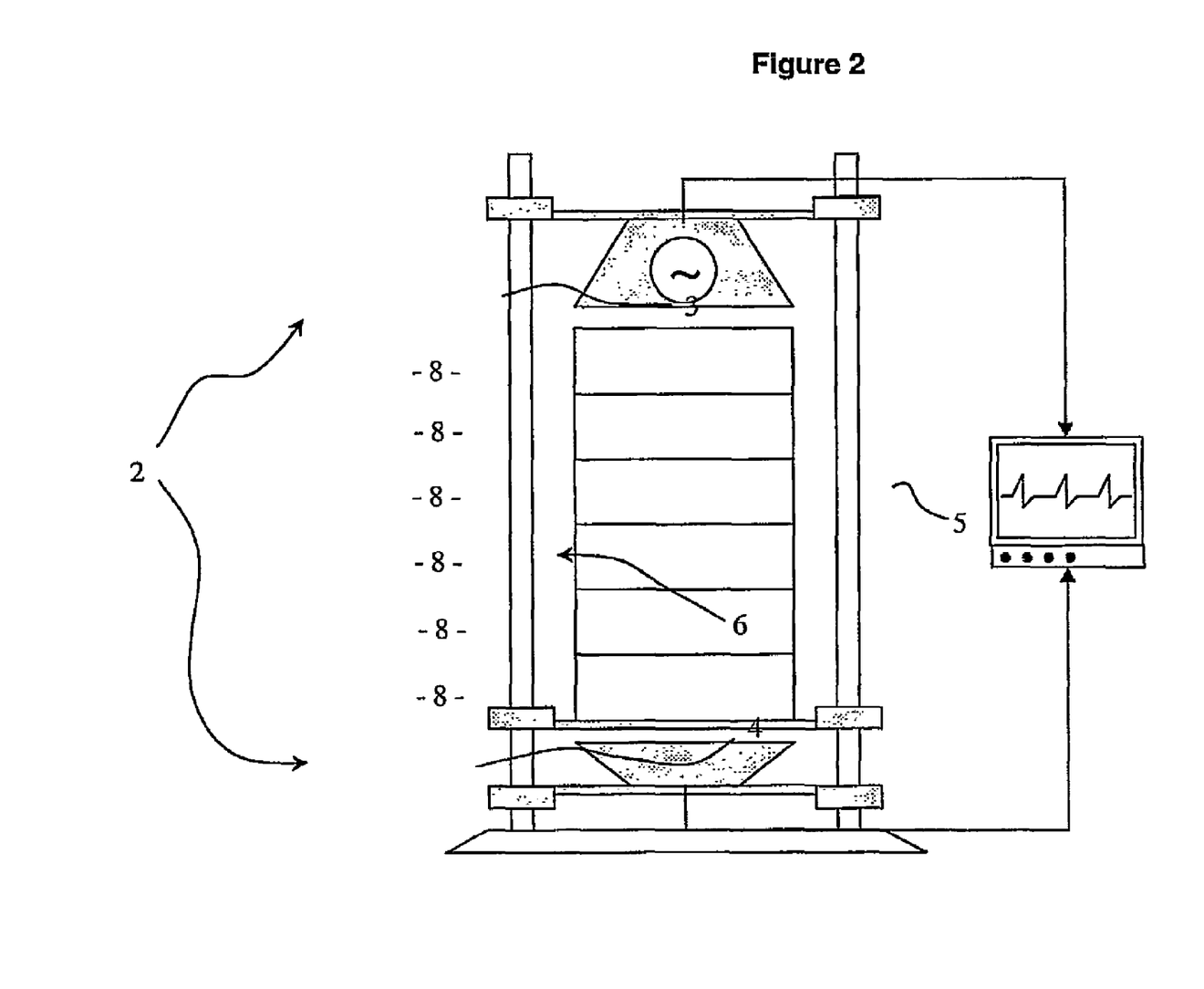
FIG. 2 shows a schematic representation of a second preferred embodiment of the present invention.

FIGS. 1-2 show exemplary embodiments of the present invention in the form of a non-invasive temperature and/or composition measurement system (1) including a transmitter and receiver mechanism (2) comprised of one or more transmitting antenna(e) (3) and receiving antenna(e) (4) and a signal processing means (5).

In the embodiment shown in FIG. 1, the system (1) is used to measure the temperature of a target (6) in the form of pallet (7) stacked with a plurality of processed meat cartons (8). The meat and placed in plastic bags inside a toughened cardboard meat carton. FIG. 1 shows a twin stack of cartons (8) on a pallet (7) positioned between the transmitter/receiver mechanism (2) for monitoring on an automated process line moving along an axis orthogonal to the plane of the paper.

It will be appreciated that the invention need not be limited to such configurations, and alternate target configurations are possible. FIG. 2 shows a second embodiment, with an alternative embodiment target (6) arrangement of a single vertical stack of cartons (8), with a corresponding vertically aligned transmitter/receiver mechanism (2).

In both embodiments, the transmitter/receiver mechanism (2) is capable of irradiating said target (6) with at least a first and a second electromagnetic radiation signal of differing frequencies and receiving an attenuated signal transmitted though the target (6). The first signal (not shown) has a frequency in the microwave spectrum, and said second signal (not shown) has a frequency in the radio frequency (RF) spectrum. The respective Microwave and RF transmissions may be emitted from a separate transmitters (3) or alternatively, by a single combination transmitter (3) capable of generating signals of both frequencies. As used herein, the term microwave spectrum or signal includes frequencies between 100 MHz-500 GHz and thus also encompasses signals with UHF frequencies, while the term radio frequency (RF) spectrum is defined as 01. KHz-100 MHz.

FIGS. 1 and 2 both show a single set of transmitter/receiver antennae (3, 4) associated with either of microwave or RF signal. A second set associated with the other of the two frequencies may be physically located:
  immediately adjacent the first antennae set (3, 4), with a signal beam path emitted in parallel to the first antennae set (3,4);
  orthogonal to the first antennae set (3, 4), with a signal beam path intersecting orthogonally to that of the first antennae set (3,4), or
  with an opposing orientation to the first antennae set (3, 4), with the transmitted beam path of the second signal travelling along a reciprocal path to the first signal.

In a further embodiment (not shown), the transmitter and receiving antennae of at least one set (3, 4) are orientated and aligned such that the receiver (4) receives a reflect signal from the target (6) and not a transmitted signal.

The attenuation of the transmitted signal will be effected by spaces between, and within, cartons (which will be "seen" by the receiver as 100% transmittance) and non-homogeneity in the target which distorts the total water content (ice and water) as "seen" by the receiver.

These potential errors pose a similar problem to that of the fat content and are theoretically eliminated by using the microwave/RF frequency ratio. However, for the ratio to be meaningful the microwaves and radio waves should travel through the same beam path.

Further potential errors may be introduced by portions of the emitted signal being received by the receiving antenna (4)

from paths other than those transmitted through the target, leading to a falsely high attenuation signal level. This may be mitigated by placing the transmitting antenna (3) and (optionally) the receiving antenna (4) directly in contact with the target (6) to avoid any signal reflections, as described more fully in the applicants co-pending application PCT/NZ03/00279.

In operation, a typical target (7) of palletised meat cartons (8) is positioned between a set of transmitting and receiving antennae (3, 4) and irradiated with microwave radiation or RF radiation and the attenuated signal passing though the target is measured and inputted to the signal processor (5). The process is repeated for the other signal. The attenuated microwave signal measurement gives an indication of the water present in the signal beam path by comparison with established data for attenuation of liquid water of the measurement, given that the beam path is known by simply measuring the target width. Similarly, the attenuated RF signal is compared to established data on ice attenuation to predict how much of the beam path is ice. The ratio of the two results gives an indication of the target temperature according to the relationship.

$$T \propto \left[ \frac{T_f}{1 - \frac{\Delta_{RF}}{\Delta_{Mw}}} \right] \quad (5)$$

where:
$T_f$ is the Freezing Temperature,
T is the Actual Temperature
$\Delta_{RF}$ Radio Frequency attenuation ($\propto$ to I, the ice fraction)
$\Delta_{Mw}$ is the Microwave attenuation ($\propto$ to the Water fraction W)

Calibration factors related to the target material, frequency, and/or system geometry are incorporated in the temperature determination to remove the proportional relationship.

In a further aspect of the present invention, the target composition fractions of some constituents such as fat may be determined. It will also be appreciated that if the target weight is known and if the water fraction W and ice fraction I are known, it will be possible to calculate the target fat content (CL) according to the relationship:

Fat mass=Target Mass×[1−[W+I+S]]

Further, a third electromagnetic frequency may be correlated to attenuation of electromagnetic energy by fat, preferably in the 100-110 MHz range. Thus by rearranging equation (6) a composition balance may be obtained:

Fat Fraction+W+I=1−S

And since

S=β(W+I)

and assuming a typical value of β≈0.2

Then

Fat Fraction=1−(1.2×[W+I])

The third frequency may be emitted from a further antennae set (not shown) distinct from the or each antennae set(s) associated with the first and second frequencies. In further embodiments, the third frequency may be emitted from a variable frequency antennae set also responsible for the first and/or second frequencies. A variety of tests and experiments were performed to validate and exemplify the present invention and extend the range of potential applications from temperature measurement of frozen biological samples inside enclosed packing containers to measuring multiple characteristics of the samples including the fat content and temperature over the chilled region. Considering these applications in turn:

1. Application of Present Invention to the Inference of Frozen Meat Temperature

This application utilises meat as the biological sample and the ice fraction as the characteristic to be measured, where the temperature of the meat is inferred mathematically from the ice fraction. To replicate typical commercial applications:

sample thicknesses of meat between 10 cm (equivalent to commercial cartons) up to 100 cm (equivalent to commercial pallets of meat) were chosen;

samples were frozen to between −10° C. and −18° C. to replicate the commercial temperature range for export frozen meat, and samples between 60 and 97% chemical lean (CL), spanning the typical range of CL commercially exported meat, were measured.

The frequency range from 1 kHz through to 300 MHz was scanned and the optimal frequencies selected for determining the ice component, water component and fat component of the meat based on the relative attenuation of each component at each frequency. The difference between the value of the real and imaginary components of the two signals is due to the attenuation and phase angle loss of the signal as it passes through a material. In particular, for this application the attenuation curves for ice and water in meat were selected as the calibration parameter.

The determination revealed optimal frequencies for said first frequency range (optimised for water absorption) of 200-400 MHz, from which a frequency of 200 MHz was selected. The optimal second frequency for ice was determined as lying in the range 0.1-10 kHz, from which a frequency of 10 kHz was selected.

Figure 3:
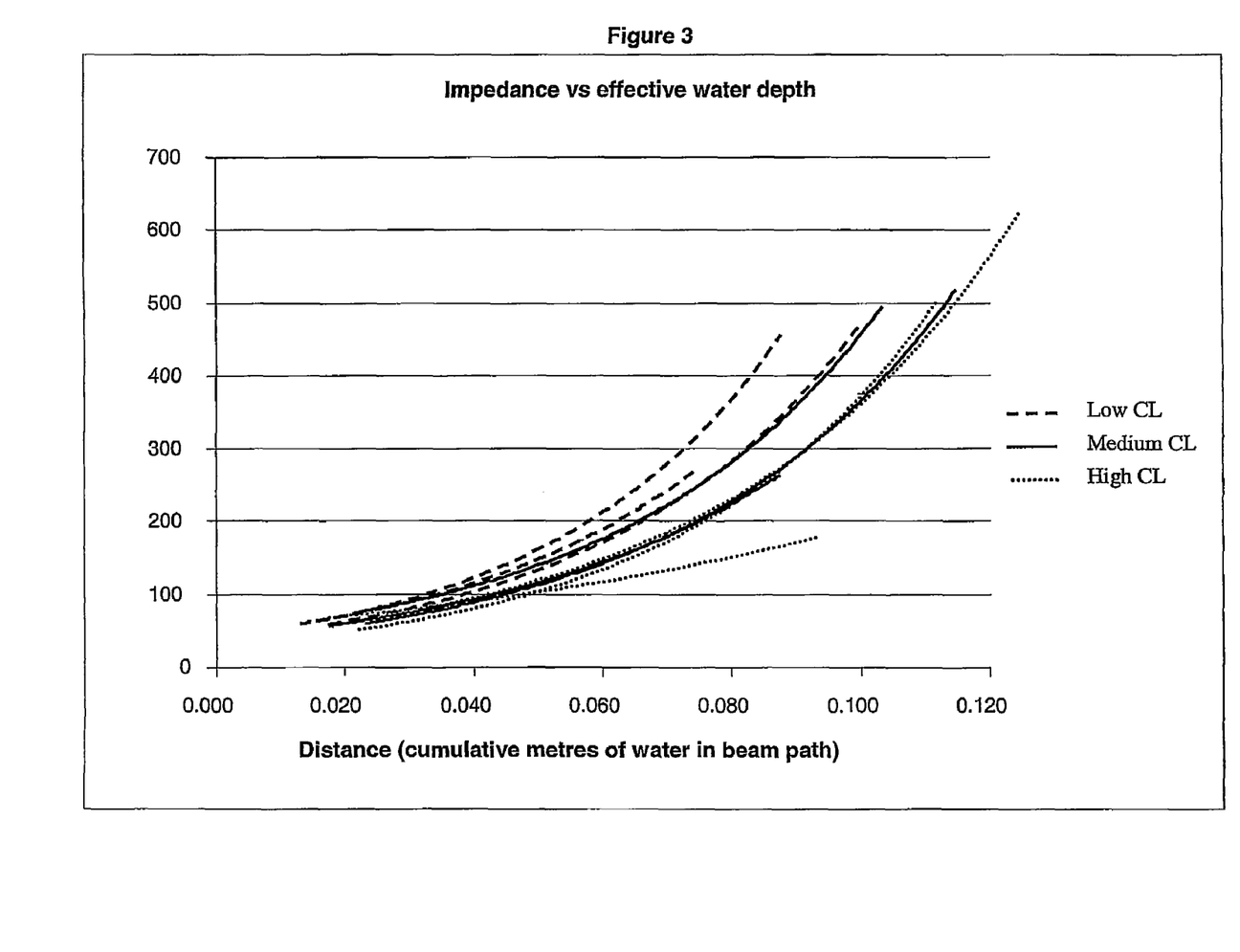
FIG. 3 shows a graph of impedance V effective water depth penetration for low, medium and high CL values.
Figure 4:
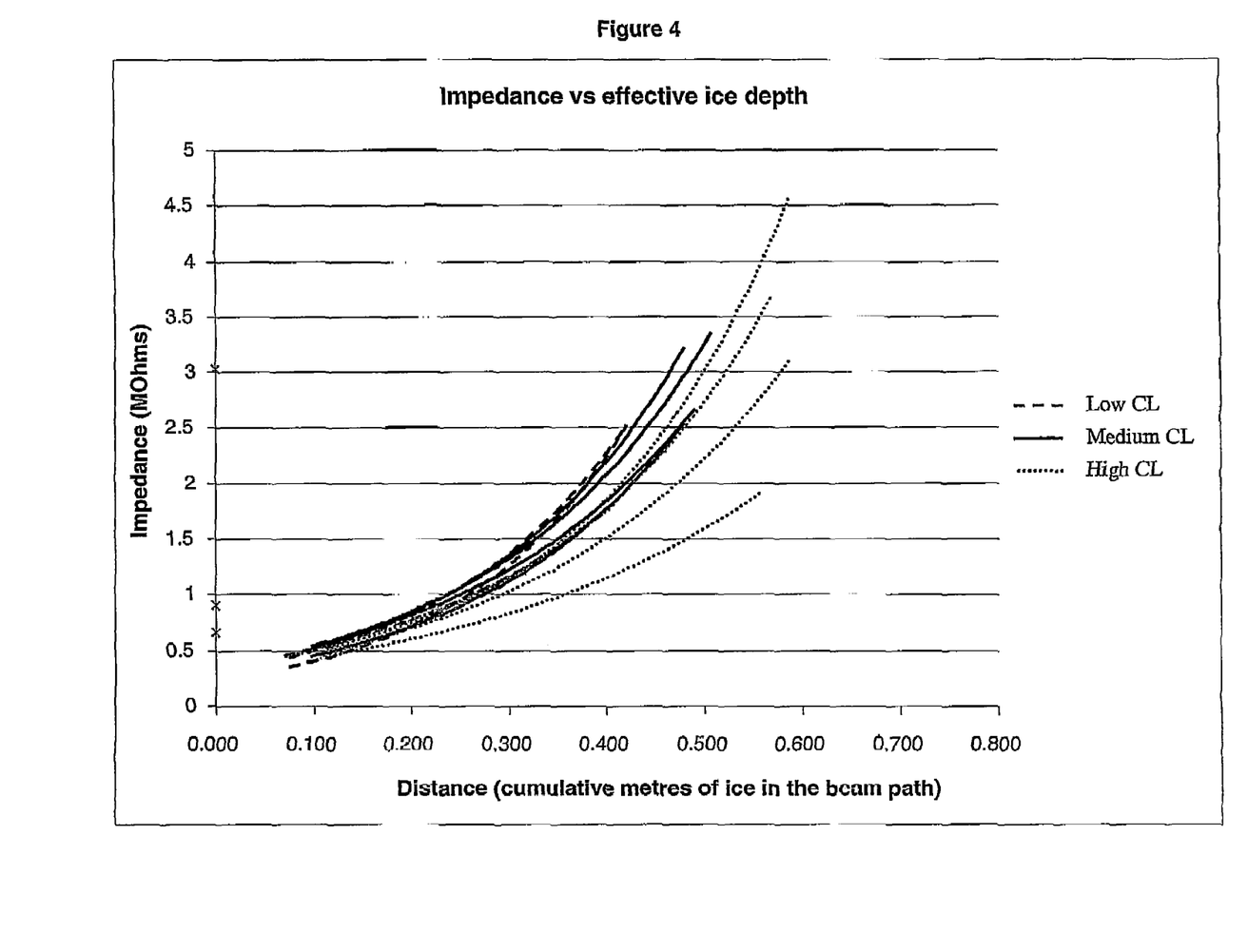
FIG. 4 shows a graph of impedance V effective ice depth penetration for low, medium and high CL values.

The samples were rescanned at the selected frequencies and the results are graphically shown in FIGS. 3 (data curves for water) and FIG. 4 (data curves for Ice) for low, medium and high CL values. Irradiation of a meat sample of 100 cm thickness at 10 kHz and 200 MHz returned impedance (X) values of:

$X_{ice}$=4.2

$X_{water}$=400

Rearranging the calibration equation 1 (without CL correction) of the curves in FIGS. 3 and 4 gives:

$$\frac{P_z}{P_o} = e^{-2\alpha z}$$

and thus, $$\text{Ln} \frac{P_z}{P_o} = -2\alpha z$$

Given $$P = X \sin\theta,$$

where θ is the phase loss angle for a given material at a given temperature.

$$Z_{ice} = \left[\frac{1}{-2\alpha_{ice}}\right] \ln \frac{X_{ice}}{X_{0_{ice}}} \quad (8a)$$

$$Z_{Water} = \left[\frac{1}{-2\alpha_{water}}\right] \ln \frac{X_{water}}{X_{0_{water}}} \quad (8b)$$

Substituting into the preceding equation and eliminating $\sin \theta$, the variables $\alpha$ and $P_0$ are solved from calibration, thus giving:

$$Z_{ice} = [1/4.20] \ln(X_{ice}/0.317) \quad (8c)$$

$$Z_{water} = [1/24.01] \ln(X_{water}/38.9) \quad (8d)$$

where Z is the equivalent thickness (in cm) of pure substance (water or ice) penetrated by the beam.

Therefore substituting X:

$$Z_{ice} = 53.5 \text{ cm}$$

$$Z_{water} = 9.7 \text{ cm}$$

Thus in the sample irradiated, the beam travelled through the equivalent of 53.5 cm of pure ice and 9.7 cm of pure water.

It follows from a meat thickness of 100 cm then:

$$I = Z_{ice}/100 = 0.539 \quad (9a)$$

$$W = Z_{water}/100 = 0.097 \quad (9b)$$

where I = Ice Fraction in the substance (meat)
W = Water Fraction in the substance (meat).

It is known that the temperature of the meat may be accurately estimated by the following equation:

$$T = \frac{(T_f + W + I)}{1 - \left[\frac{I}{0.9375(W+I)}\right]} \quad (10)$$

Where T is the temperature of the meat
$T_f$ is the temperature at which the meat begins to freeze
I is the Ice Fraction
W is the water fraction Assuming a representative valve for $T_f = -1.8°$ C., and substituting I and W from equation 9a and 9b then:

$$T = \frac{(-1.8 + 0.97 + .539)}{1 - \left[\frac{0.539}{0.9375(0.97 + 0.539)}\right]}$$

$$= -12.1°C.$$

Given an estimated error of prediction of $\pm 3°$ C. without CL correction (for 95% confidence level) the inferred temperature correlated well with the actual temperature of the meat measured as approximately $-13 \pm 0.5$.

2. Application of Present Invention to the Inference of the Chemical Lean (CL) Ratio of Frozen Meat.

The Chemical Lean [ratio] of meat may be defined as the ratio of lean meat in a sample of meat. Primarily determined chemically (giving rise to the name) by solvent extraction of the fat and calculating the weight difference of the residue over the original sample weight. However this is a labour intensive, slow and potentially hazardous test that is performed in a laboratory where inter-operator errors are evident.

Utilising the present invention, the CL can be determined according to as follows:

Method 1

As given previously in equation (7), the Fat fraction F is given as $$F + W + I = 1 - S$$

For lean meat, the Fat Fraction is also:

$$CL = 1 - F \quad (11a)$$

since, by definition, the "lean" is the residue after the fat is removed.

Thus, $$CL = (1+S) \times (I+W) \quad (1b)$$

Thus, taking a typical Solids Fraction value of S=0.25 and using the data from equations 9a and 9b, then $$CL = 1.25(0.535 + 0.097)$$

$$= 0.79.$$

The assumed value of S introduces an error of approximately $\pm 2\%$.

Method 2

Fat is known to contain small quantities of water which are bound into the fat structure and are therefore not free to rotate as does "free water". This "bound water" is known to have a rotational harmonic occurring between 1 and 100 MHz.

Figure 5:
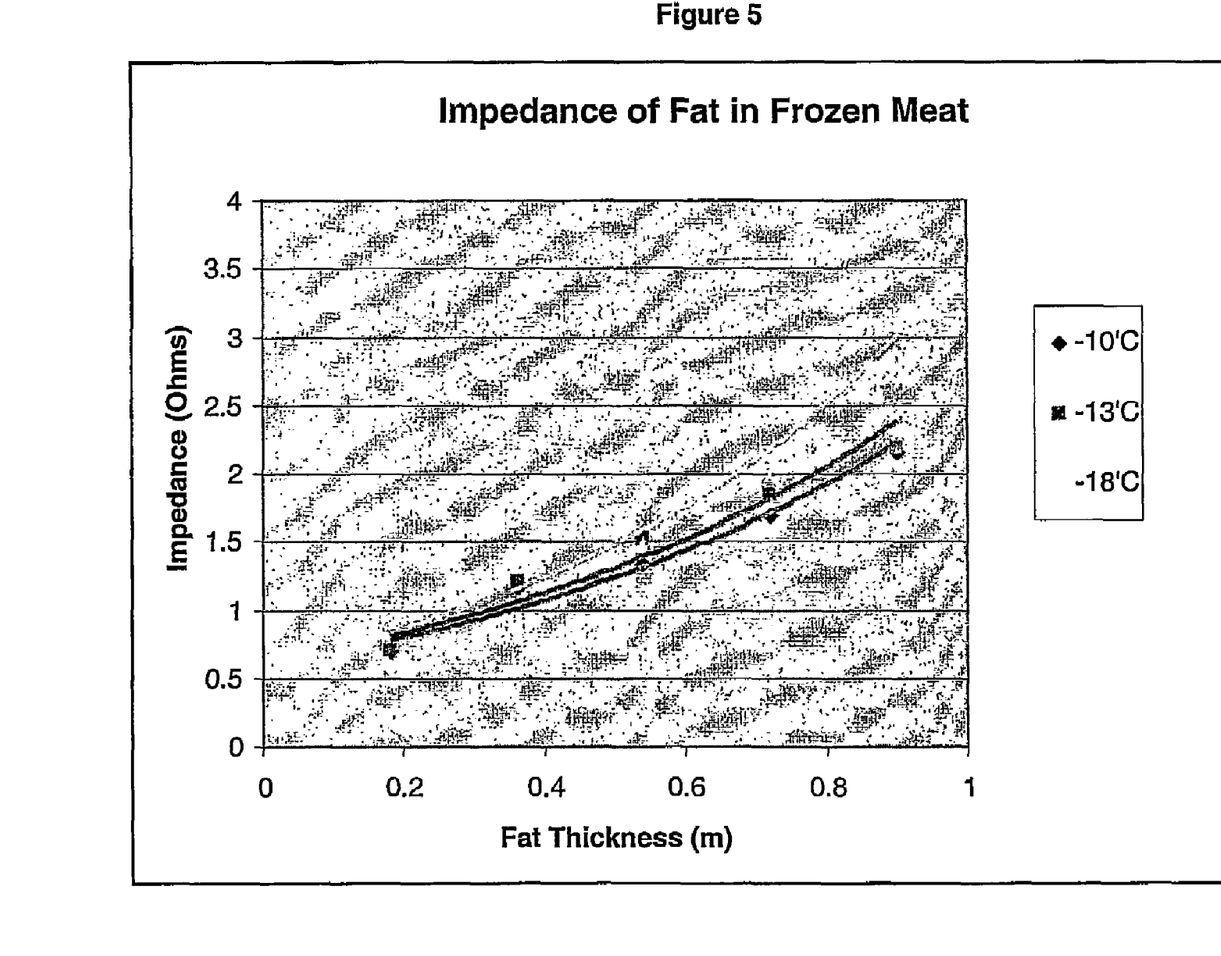
FIG. 5 shows a graph of impedance V fat depth in frozen meat at −10, −13, and 18° C.

A typical calibration curve is shown in FIG. 5. From the curves in FIG. 5, the equivalent fat thickness of the irradiated sample can be determined and inserted into the equation:

$$F = Z_{fat}/\text{sample thickness} \quad (9c)$$

to determine fat fraction F.

Substituting in equation (5):

$$CL = 1 - Z_{fat}/\text{sample thickness} \quad (11a)$$

enables the CL to be calculated for a known sample thickness.
Thus by introducing a third frequency, it is possible to:
determine the temperature and the CL of the frozen sample
the CL of non-frozen meat, or oils, butter etc.

2. Application of Present Invention to the Inference of the Temperature of Chilled Product.

The present invention may also be used to infer temperature of product in the chilled range. Considering a meat/fat material as the target sample, FIGS. 6 and 7 show the temperature of fat and meat constituents through the chilled temperature range for different irradiating frequencies.

The phase loss angle of signals passing through materials is related to the temperature of the sample (Brengsston et al, J.

Sci. Fd Agric 1963 Vol14 August). Further, Brengsston et al also demonstrated that each material causes a different loss angle at a given temperature, and therefore in non-homogeneous materials, such as meat, the loss angles of each material are convolved. Thus for the chilled temperature to be inferred effectively, the loss angle of each material needs to be determined for all components before the temperature can be derived.

Figure 6:
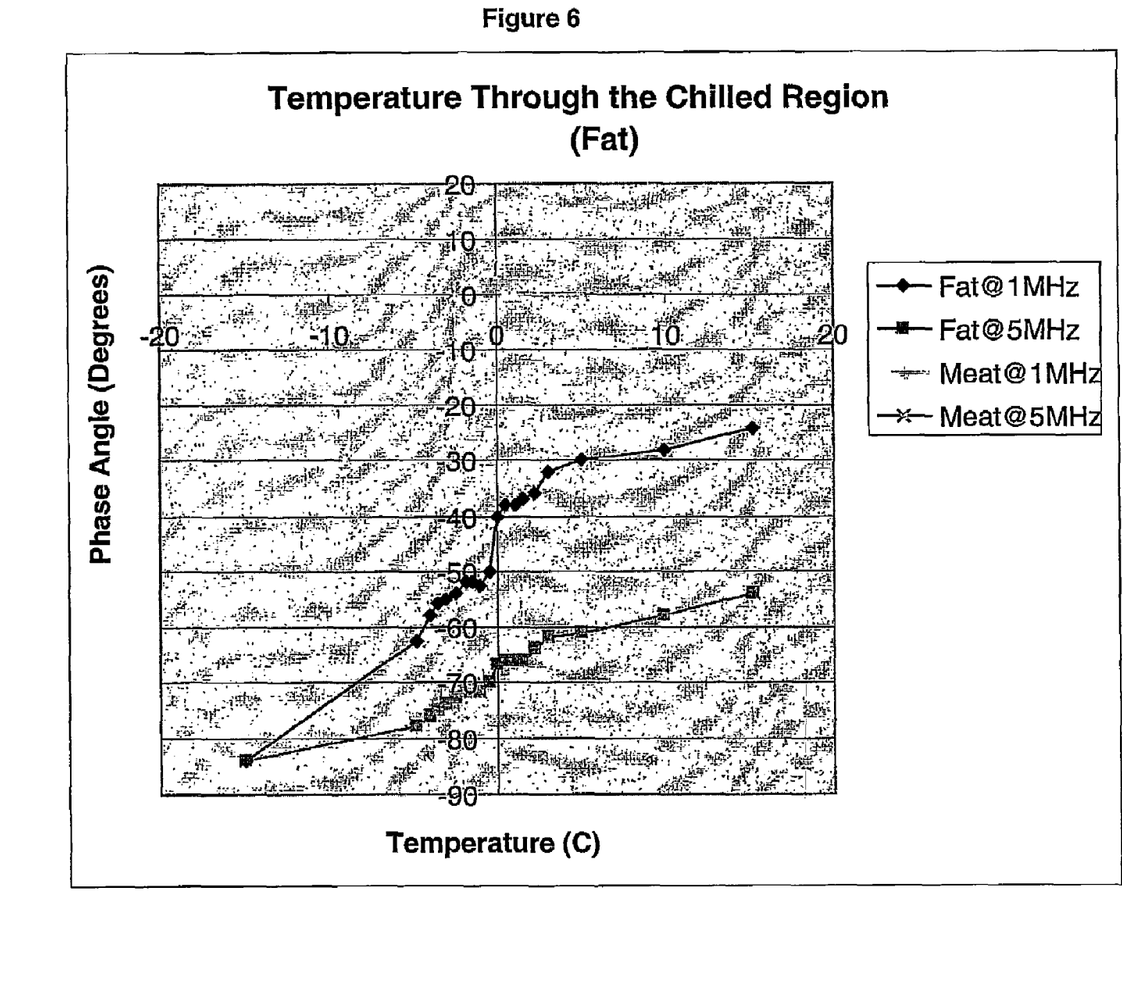
FIG. 6 shows a graph of phase angle V target temperature for fat and meat through the chilled region at 1 MHz and 5 MHz.
Figure 7:
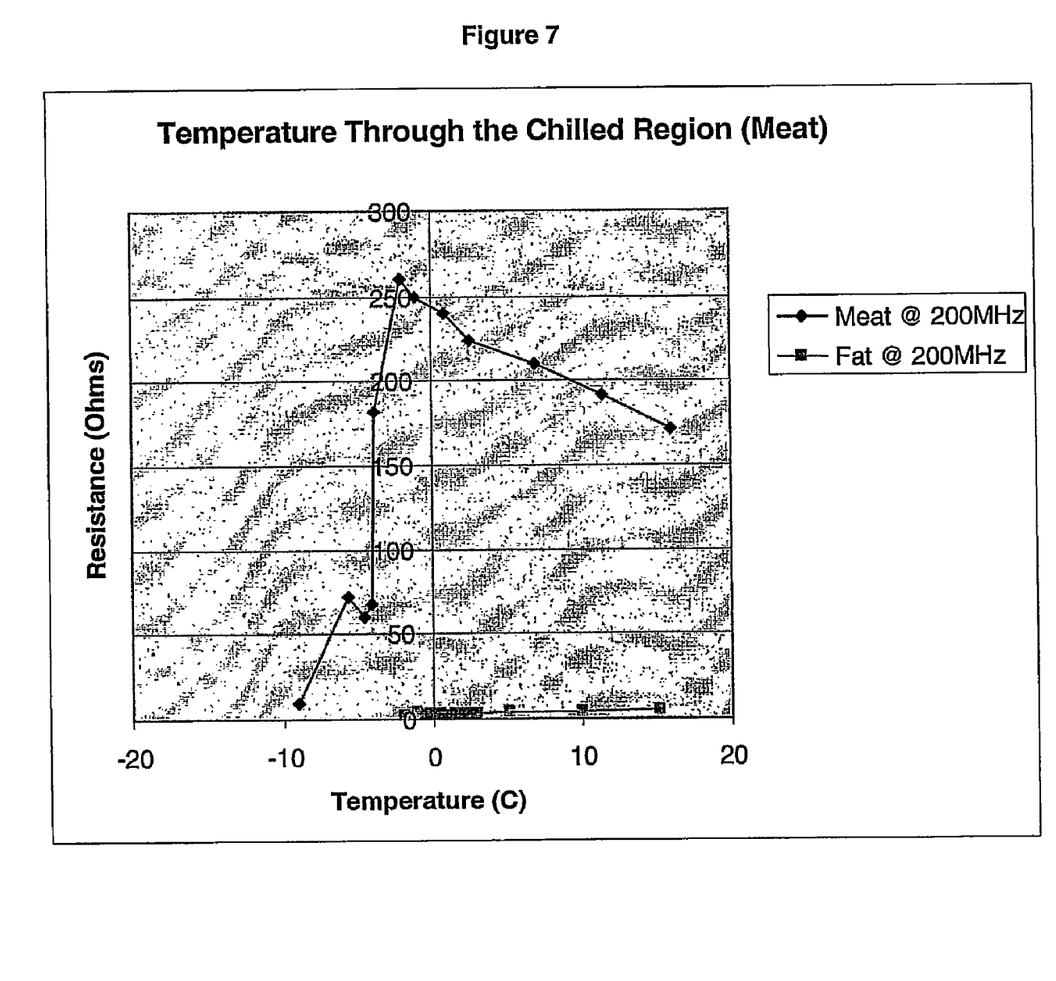
FIG. 7 shows a graph of phase angle V target temperature for fat and meat at 200 MHz through the chilled region.

FIGS. 6 and 7 show data tracking the temperature of meat and fat though the chilled temperature range at 1 & 5 MHZ and at 200 MHz respectively, obtained using a concentric Radio Frequency test chamber. As may be seen in FIG. 6 for example, at temperatures in the chilled region (i.e. above zero), the phase loss angle or attenuation for meat (particularly at an irradiating frequency of 1 MHz) is negligible, and may effectively be ignored. Consequently, the measured phase loss angle provides a direct measure of the Fat constituent temperature. Although the response at an irradiating frequency of 1 MHz, for meat is non-zero, however is still substantially linear above zero degrees and may thus be offset as a constant.

Thus, a frequency of 1-5 MHz, (preferably 5 MHz) provides an effective means of determining the chilled temperature of fat for the small sample target of approximately 50 mm. As discussed above, the optimum frequency would need to be altered for thicker samples, as given by equation 1.

It can also be seen, that as the temperature falls below at approximately −3° C. and the target freezes, the resultant combined phase angle/attenuation measured from the fat and meat gives a convolved result which cannot be distinguished into its components without use of a third frequency.

FIG. 7 shows the results of irradiating at a frequency of 200 MHz, which gives a negligible response for fat at chilled temperatures, thus enabling the meat temperature to be measured directly from the resultant attenuation measured. Again, these frequencies relate to the 500 mm small sample used and differing frequencies would be selected for differing target thicknesses.

Thus by carefully selecting, in this case, two frequencies the convolving effect of each material on the other can be virtually eliminated and the temperature of each material inferred from the calibration curve.

It can be seen that using the above-described principles of the present invention, the chilled temperature of almost any biological material can be determined.

Aspects of the present invention have been described by way of example only and it should be appreciated that modifications and additions may be made thereto without departing from the scope thereof.

The invention claimed is:

1. A method of temperature and/or composition measurement of an at least partially aqueous target using a system including:
   a transmitter and receiver mechanism including one or more transmitting and receiving antenna(e);
   signal processing means, capable of calculating the attenuation of the transmitted signal;
   said method including:
   irradiating said target with a plurality of electromagnetic radiation signals including at least first and second electromagnetic radiation signals of differing frequencies wherein said first signal has a first frequency in the microwave/UHF spectrum, and said second signal has a second frequency in the radio frequency (RF) spectrum;
   receiving an attenuated signal transmitted though the target;
   calculating the attenuation of the transmitted signal with said signal processing means; and
   wherein a fat mass of the target with a known target mass, a solids fraction (S) and with a water fraction (W) and ice fraction (I) proportional to attenuations of said first frequency and second frequency respectively, is calculated by applying said fractions according to the relationship:

Fat Mass=Target Mass×[1−[W+I+S]].

2. A method as claimed in claim 1, wherein the solids fraction (S) is determined from known data tables.

3. A method as claimed in claim 1, wherein a fat fraction (F) composition of the target is calculated independent of the target temperature and mass according to the relationship:

F+(1+β)×[W+I]=1 where β is a proportionality constant.

4. A method of temperature and/or composition measurement of an at least partially aqueous target using a system including:
   a transmitter and receiver mechanism including one or more transmitting and receiving antenna(e);
   signal processing means, capable of calculating the attenuation of the transmitted signal;
   said method including:
   irradiating said target with a plurality of electromagnetic radiation signals including at least first and second electromagnetic radiation signals of differing frequencies wherein said first signal has a first frequency in the microwave/UHF spectrum, and said second signal has a second frequency in the radio frequency (RF) spectrum;
   receiving an attenuated signal transmitted though the target;
   calculating the attenuation of the transmitted signal with said signal processing means; and
   wherein a chemical lean (CL) of a target with a solids fraction (S) and with a water fraction (W) and ice fraction (I) proportional to attenuations of said first frequency and second frequency respectively, is calculated by applying said fractions according to the relationship:

CL=(1+S)×(I+W).

5. A method of temperature and/or composition measurement of an at least partially aqueous target using a system including:
   a transmitter and receiver mechanism including one or more transmitting and receiving antenna(e);
   signal processing means, capable of calculating the attenuation of the transmitted signal;
   said method including:
   irradiating said target with a plurality of electromagnetic radiation signals including at least first and second electromagnetic radiation signals of differing frequencies wherein said first signal has a first frequency in the microwave/UHF spectrum, and said second signal has a second frequency in the radio frequency (RF) spectrum;
   receiving an attenuated signal transmitted though the target;
   calculating the attenuation of the transmitted signal with said signal processing means; and
   wherein a chemical lean (CL) of a target with a sample thickness (t) is calculable by irradiating the target with at least a third electromagnetic radiation signal of differing frequency to said first and second frequencies and receiving an attenuated signal $Z_{fat}$ transmitted though the target, is calculated according to the relationship:

CL=1−$Z_{fat}$/t.

6. A method of temperature and/or composition measurement of an at least partially aqueous target using a system including:

a transmitter and receiver mechanism including one or more transmitting and receiving antenna(e);

signal processing means, capable of calculating the attenuation of the transmitted signal;

said method including:

irradiating said target with a plurality of electromagnetic radiation signals including at least first and second electromagnetic radiation signals of differing frequencies wherein said first signal has a first frequency in the microwave/UHF spectrum, and said second signal has a second frequency in the radio frequency (RF) spectrum;

receiving an attenuated signal transmitted though the target;

calculating the attenuation of the transmitted signal with said signal processing means; and wherein said first and second signals are transmitted from separate antennae along reciprocal beam axes from opposing sides of the target.

* * * * *